United States Patent [19]

Chiba

[11] 4,325,965

[45] Apr. 20, 1982

[54] AGENT FOR PREVENTING OR TREATING PSORIASIS

[75] Inventor: Ryoichi Chiba, Tokyo, Japan

[73] Assignee: Eisai Co., Ltd., Tokyo, Japan

[21] Appl. No.: 198,560

[22] Filed: Oct. 20, 1980

[30] Foreign Application Priority Data

Oct. 22, 1979 [JP] Japan ................................ 54/135136

[51] Int. Cl.$^3$ ........................................... A61K 31/355
[52] U.S. Cl. .................................................. 424/284
[58] Field of Search ......................................... 424/284

[56] References Cited

U.S. PATENT DOCUMENTS 4,181,725 1/1980 Voorhees et al. ................... 424/258

*Primary Examiner*—Leonard Schenkman
*Attorney, Agent, or Firm*—Blanchard, Flynn, Thiel, Boutell & Tanis

[57] ABSTRACT

Psoriasis is treated with δ-tocopherol or ester thereof.

5 Claims, No Drawings

AGENT FOR PREVENTING OR TREATING PSORIASIS

The present invention relates to a method for treating psoriasis. More particularly, the present invention relates to a method for treating psoriasis with a composition containing δ-tocopherol or an ester thereof, as the effective ingredient.

Psoriasis is chronic inflammatory keratodermia which causes clear erythema with silver-white mica-like scales on the skin of a human being at various locations, such as at the elbow, knee, scalp, back and waist.

This dermatitis is quite difficult to cure. Even if it is superficially cured once, it may soon return repeatedly. Psoriasis is a common dermatitis in countries in Europe and in America. Also in Japan, the number of psoriasis patients has recently increased rapidly.

Generally, the term "psoriasis" indicates psoriasis vulgaris in many cases. The term "psoriasis" also includes arthritic psoriasis, psoriasis figurata and psoriasic erythrodermia. The term "psoriasis" used herein includes not only psoriasis vulgaris, but also all other types of psoriasic diseases.

Although it is said that psoriasis is caused by contagion or from an external wound or stress, the etiological causes thereof are still unknown. Therefore, no fundamental therapy has been established yet and patients have suffered from the disease for a long period of time.

The principal medicines currently used for the medicinal therapy of this disease are corticosteroids for external use. Although they are effective for palliative treatment of psoriasis, corticosteroids are unsuitable for long-term use because they produce unfavorable side effects and the disease returns soon after their use is discontinued.

More particularly, when the corticosteroids for external use are used, the psoriasis lesions disappear rapidly, but psoriasis frequently returns soon after such use is discontinued. In many cases of the return of psoriasis, the lesions are more serious with respect to both area and strength, compared with those observed in the initial stage. Further, in the skin tissue after the disappearance of the lesion, an abnormal change of capillary-papillae to a morbid state, which is peculiar to psoriasis, still remains in almost all cases. Thus, a palliative treatment is effected and a cure is not achieved.

The unfavorable side effects of corticosteroids include vasodilation (capillaries), skin atrophy and the concurrence of infectious diseases. If corticosteroids are administered continuously for a long period of time, the influences thereof on the whole body pose problems.

In view of the circumstances set forth above, the development of a new treatment for psoriasis, which treatment is free of unfavorable side effects and which can be used continuously for a long period of time, has been sought eagerly. After years of intensive investigations, the inventor has found, surprisingly in view of the prior art, that this goal can be attained by using δ-tocopherol or an ester thereof as the effective ingredient.

Therefore, the object of the present invention is to provide a method for prophylactic and therapeutic treatment of psoriasis, which method can be used continuously for a long period of time, substantially without exhibiting unfavorable side effects.

The effective ingredients used in the present invention are δ-tocopherol and esters thereof, such as the acetic acid ester and the succinic acid ester thereof.

δ-Tocopherol, which also is called 8-methyltocol from the viewpoint of its chemical structure, is a member of the vitamin E group of compounds. From the viewpoint of its chemical structure, δ-tocopherol can be divided into d-δ-tocopherol, l-δ-tocopherol and dl-δ-tocopherol. According to the present invention, any one of them and esters thereof, or mixtures of at least two of them or their esters can be used. Among the above-mentioned δ-tocopherol compounds, natural d-δ-tocopherol or synthetic dl-δ-tocopherol is most suitable for use in the present invention. d-δ-Tocopherol is usually extracted from vegetable oils such as soybean oil, sesame oil and wheat germ oil. Recently, however, methods of synthesizing the same have been developed. d-δ-Tocopherol is a slightly yellowish oil (see Merck Index, Ninth Edition, pp. 1221–1222).

δ-Tocopherol, used in the present invention, has scarcely been used heretofore in or on human bodies because of its low vitamin E biological activity.

The present invention has been completed on the basis of the discovery that δ-tocopherol is quite effective for treating psoriasis. Although the mechanism has not been elucidated yet, it is considered that the effects of δ-tocopherol are related to the antioxidation property thereof. Thus, δ-tocopherol is a treatment for psoriasis which exhibits a new working mechanism completely different from that of the corticosteroids which have been used heretofore.

In carrying out the present invention, δ-tocopherol is used externally (topically) in any desired form. Generally, it is dissolved in a suitable liquid (e.g., a solvent), or dispersed or emulsified in a medium in a conventional manner to form a liquid preparation for external use or it is mixed with a suitable solid topical carrier to form an ointment or cream. As the solid carriers, there can be mentioned oily substances such as liquid paraffin, solid paraffin, petrolactum, squalane, palmitic acid, stearic acid, cetanol, stearyl alcohol, isopropyl myristate, coconut oil, olive oil, peanut oil, castor oil, sesame oil, lard, beef tallow, hardened castor oil, bees wax, carnauba wax, spermaceti, lanolin, acetoglyceride and silicone oil. If necessary, an emulsifier, dispersing agent, wetting agent and stabilizer can be added suitably thereto to obtain a desired ointment, cream or the like.

The concentration of the effective ingredient, i.e. δ-tocopherol or its ester, in the composition for external use is not particularly limited. Generally, however, the concentration of δ-tocopherol or its ester is about 0.1–5 wt.%, preferably about 0.5–3 wt.%, particularly around 0.5 wt.%, based on the total weight of the composition.

The effective dosage of the treating composition for external use, according to the present invention, is not critically limited, but rather it is variable depending on the type of psoriasis to be treated, the condition of the patient and the magnitude of the lesions. Generally, the condition of the patient is improved by the application of the composition to the affected part several times a day. For example, the effective dose of δ-tocopherol for psoriasis is generally about 50–100 mg/day. However, this is merely the common dosage for most patients. The dosage is variable widely depending on the condition of the patient.

The acute toxicity of d-δ-tocopherol used in the present invention was examined using Slc-ICR mice (7–8 weeks old) and Slc-SD rats (7–8 weeks old). The results are shown in the following Table 1.

TABLE 1

| | LD$_{50}$ (g/Kg) | | | |
|---|---|---|---|---|
| | Species | | | |
| | Mice | | Rats | |
| Administra- | Sex | | | |
| tion Route | Male | Female | Male | Female |
| Peroral | 15 | 15 | 15 | 15 |
| Intra-abdominal | 4.20 | 7.90 | 4.13 | 3.10 |

It is apparent from Table 1 that δ-tocopherol, used in the present invention, is quite safe and is suitable for treatment of patients who require long-term, continuous therapy.

The following experimental examples further illustrate the effects of the present invention.

EXPERIMENTAL EXAMPLES

1. Test method:

(1) Treating compositions tested:

Compositions were used comprising the following effective ingredients incorporated in an O/W type emulsion base. For comparison, in Table 4, α-tocopherol, which is a typical vitamin E compound, was also used.

(1) Cream free of d-δ-tocopherol (i.e. only the emulsion base was used), (2) Cream containing 0.5 wt.% of d-δ-tocopherol, (3) Cream containing 1 wt.% of d-δ-tocopherol, (4) Cream containing 3 wt.% of d-δ-tocopherol, (5) Cream containing 0.5 wt.% of d-α-tocopherol (comparison), (6) Cream containing 0.5 wt.% of dl-α-tocopherol (comparison), (7) Cream containing 3 wt.% of d-α-tocopherol (comparison), and (8) Cream containing 3 wt.% of dl-α-tocopherol (comparison).

(2) Subjects to be treated:

Patients suffering from psoriasis.

(3) Method of external application:

In all cases, the O.D.T. method (wherein the composition is rubbed well into the affected part and then a film of Saran Wrap or the like is applied thereto closely) was employed in the nighttime and the S.A. (simple application) method was effected twice in the daytime. The affected parts to which the test samples were to be applied were selected so that they exhibited as closely similar conditions as possible and the remedies could be applied according to the above methods of application in order that the effects of the compositions could be compared with one another.

(4) Observation points and criteria of the effects:

(i) The condition of the skin of each patient was judged from the scales, redness, infiltration and hypertrophy. The overall degree of seriousness of the psoriasis was evaluated by applying rankings of +++ (quite serious), ++ (medium), + (light), ± (slight) and − (no symptom). The results of the evaluation of the psoriasis after treatment were compared with the condition before the treatment. The term "improved" in the following Tables 2 and 3 indicates that the condition was improved by at least one ranking after the treatment in the case of Table 2 and by at least two rankings in the case of Table 3. Non-improved cases are indicated as "unchanged" or "worsened", accordingly.

(ii) In the case of Table 4, the rate of overall improvement was judged from the change between the symptoms before the treatment and those after the treatment and is shown in 5 rankings of 1 (the lesion disappeared or was remarkably improved), 2 (fairly improved), 3 (slightly improved), 4 (unchanged) and 5 (rather worsened).

(5) Times of observation and judgement:

As a rule, the subjects were observed before the treatment and after the treatment was performed for 2 and 4 weeks.

(6) Concurrent medicines:

As a rule, no other medicine was applied to the affected part to be tested, but other external therapies were allowed for lesions of parts other than the part to be tested.

2. Clinical results:

(1) Degree of improvement in the condition of the skin after the application of cream containing d-δ-tocopherol:

The degrees of improvement in scales, redness, infiltration and hypertrophy, which are the symptoms most characteristic of psoriasis, after the treatment as compared with those before the treatment, are summarized into two groups, i.e. groups of "improvement by at least one rank" and "improvement by at least two ranks". The results are shown in following Tables 2 and 3, respectively. In Tables 2 and 3, S.A. indicates the simple application method and O.D.T. has the same meaning as described above. In the numerals in the tables, the denominators represent the total number of cases and the numerators represent numbers of the corresponding cases. The numerals in the parentheses represent percentages.

TABLE 2

Degree of improvement in the condition of the skin (improvement by at least one ranking after the treatment)

| Concentration of d-δ-tocopherol (wt. %) | Method of external application | Skin Condition | 2 weeks after the initiation of the treatment | | |
|---|---|---|---|---|---|
| | | | Improved (%) | Unchanged (%) | Worsened (%) |
| 0% (only the base) | S. A. + O. D. T. | Scales | 8/35 (22.8) | 25/35 | 2/35 |
| | | Redness | 4/37 (10.8) | 31/37 | 2/37 |
| (Comparison) | | Infiltration, hypertrophy | 9/34 (26.5) | 24/34 | 1/34 |
| 0.5% | S. A. + O. D. T. | Scales | 16/36 (44.4) | 20/36 | 0/36 |
| | | Redness | 12/36 | 23/36 | 1/36 |

TABLE 2-continued

Degree of improvement in the condition of the skin (improvement by at least one ranking after the treatment)

| | | | | | |
|---|---|---|---|---|---|
| (Invention) | | Infiltration, hypertrophy | (33.3) 16/35 (45.7) | 19/35 | 0/35 |
| 1% | S. A. + O. D. T. | Scales | 7/22 (31.8) | 14/22 | 1/22 |
| | | Redness | 5/23 (21.7) | 17/23 | 1/23 |
| (Invention) | | Infiltration, hypertrophy | 7/23 (30.4) | 16/23 | 0/23 |
| 3% | S. A. + O. D. T. | Scales | 14/39 (35.9) | 25/39 | 0/39 |
| | | Redness | 11/39 (28.2) | 27/39 | 1/39 |
| (Invention) | | Infiltration, hypertrophy | 13/38 (34.2) | 25/38 | 0/38 |

| Concentration of d-δ-tocopherol (wt. %) | Method of external application | Skin Condition | 4 weeks after the initiation of the treatment | | |
|---|---|---|---|---|---|
| | | | Improved (%) | Unchanged (%) | Worsened (%) |
| 0% (only the base) | S. A. + O. D. T. | Scales | 15/35 (42.9) | 18/35 | 2/35 |
| | | Redness | 11/37 (29.7) | 23/37 | 3/37 |
| (Comparsion) | | Infiltration, hypertrophy | 15/34 (44.1) | 18/34 | 1/34 |
| 0.5% | S. A. + O. D. T. | Scales | 28/36 (77.8) | 8/36 | 0/36 (0) |
| | | Redness | 26/36 (72.2) | 10/36 | 0/36 (0) |
| (Invention) | | Infiltration, hypertrophy | 27/35 (77.1) | 8/35 | 0/35 (0) |
| 1% | S. A. + O. D. T. | Scales | 14/22 (63.6) | 8/22 | 0/22 (0) |
| | | Redness | 16/23 (69.6) | 7/23 | 0/23 (0) |
| (Invention) | | Infiltration, hypertrophy | 15/23 (65.2) | 8/23 | 0/23 (0) |
| 3% | S. A. + O. D. T. | Scales | 25/39 (64.1) | 14/39 | 0/39 (0) |
| | | Redness | 24/39 (61.5) | 15/39 | 0.39 (0) |
| (Invention) | | Infiltration, hypertrophy | 25/38 (65.8) | 13/38 | 0/38 (0) |

TABLE 3

Degree of improvement in the condition of the skin (improvement by at least two rankings after the treatment)

| Concentration of d-δ-tocopherol (wt. %) | Method of external application | Skin Condition | 2 weeks after the initiation of the treatment | | |
|---|---|---|---|---|---|
| | | | Improved (%) | Unchanged (%) | Worsened (%) |
| 0% (only the base) | S. A. + O. D. T. | Scales | 4/35 (11.4) | 29/35 | 2/35 |
| | | Redness | 2/37 (5.4) | 32/37 | 2/37 |
| (Comparison) | | Infiltration, hypertrophy | 5/34 (14.7) | 28/34 | 1/34 |
| 0.5% | S. A. + O. D. T. | Scales | 11/36 (30.6) | 25/36 | 0/36 |
| | | Redness | 9/36 (25.0) | 26/36 | 1/36 |
| (Invention) | | Infiltration, hy- | 12/35 | 23/35 | 0/35 |

TABLE 3-continued

| | | | Degree of improvement in the condition of the skin (improvement by at least two rankings after the treatment) | | |
|---|---|---|---|---|---|
| 1% | S. A. + O. D. T. | pertrophy Scales | (34.3) 5/22 (22.7) | 16/22 | 1/22 |
| | | Redness | 3/23 (13.0) | 19/23 | 1/23 |
| (Invention) | | Infiltration, hypertrophy | 6/23 (26.1) | 17/23 | 0/23 |
| 3% | S. A. + O. D. T. | Scales | 8/39 (20.5) | 31/39 | 0/39 |
| | | Redness | 5/39 (12.8) | 33/39 | 1/39 |
| (Invention) | | Infiltration, hypertrophy | 9/38 (23.7) | 29/38 | 0/38 |

| Concentration of d-δ-tocopherol (wt. %) | Method of external application | Skin Condition | 4 weeks after the initiation of the treatment | | |
|---|---|---|---|---|---|
| | | | Improved (%) | Unchanged (%) | Worsened (%) |
| 0% | S. A. + O. D. T. | Scales | 10/35 (28.6) | 23/35 | 2/35 |
| | | Redness | 8/37 (21.6) | 26/37 | 3/37 |
| (Comparison) | | Infiltration, hypertrophy | 11/34 (32.3) | 22/34 | 1/34 |
| 0.5% | S. A. + O. D. T. | Scales | 24/36 (66.7) | 12/36 | 0/36 |
| | | Redness | 23/36 (63.9) | 13/36 | 0/36 |
| (Invention) | | Infiltration, hypertrophy | 23/35 (65.7) | 12/35 | 0/35 |
| 1% | S. A. + O. D. T. | Scales | 11/22 (50.0) | 11/22 | 0/22 |
| | | Redness | 12/23 (52.2) | 11/23 | 0/23 |
| (Invention) | | Infiltration, hypertrophy | 13/23 (56.5) | 10/23 | 0/23 |
| 3% | S. A. + O. D. T. | Scales | 19/39 (48.7) | 20/39 | 0/39 |
| | | Redness | 18/39 (46.2) | 21/39 | 0/39 |
| (Invention) | | Infiltration, hypertrophy | 19/38 (50.0) | 19/38 | 0/38 |

(i) Improvement by "at least one ranking" (Table 2):

The degree of improvement obtained with 0.5 wt.% of the effective component (d-δ-tocopherol) was superior to those obtained with 0 wt.%, 1 wt.% and 3 wt.% thereof after the treatment for 2 weeks with respect to all of the skin conditions. After the treatment for 4 weeks, the difference in the degree of improvement between 0.5 wt.% and 0 wt.% (only the base) was particularly significant, although an increase in the degree of improvement was obtained with all the concentrations. With respect to redness, significant differences were recognized in the cases of using 1 wt.% and 3 wt.% thereof as compared with the case of using only the base.

(ii) Improvement by "at least two rankings" (Table 3):

The cases shown in Table 2 in which the improvement was only one ranking, are included herein as members of the "unchanged" cases. That is, the cases shown in Table 3 as "improved" are those which improved by two rankings or more.

According to the evaluation effected after the treatment for 2 weeks, the improvement with 0.5 wt.% of the effective ingredient was the highest, like the results shown in Table 2. After the treatment for 4 weeks, the difference in the degree of improvement between 0.5 wt.% and 0 wt.% was particularly significant, although increases in the degree of improvement in scales, redness, infiltration and hypertrophy was obtained with all the concentrations. With respect to redness, significant differences were recognized in the cases of using 1 wt.% and 3 wt.% thereof, as compared with the case of using 0 wt.% thereof (only the base).

(2) Degree of overall improvement in Table 4:

The degree of overall improvement was evaluated from the change in the psoriasis lesions (scales, redness, infiltration and hypertrophy) and appearance of unfavorable side effects. The results are evaluated by employing 5 rankings of 1 (the lesion disappeared or was remarkably improved), 2 (fairly improved), 3 (slightly improved), 4 (unchanged) and 5 (rather worsened).

The results are shown in Table 4.

In Table 4, the clinical results obtained by using d-α-tocopherol and dl-α-tocopherol under the same conditions as in case of using d-δ-tocopherol, are shown as comparative examples. In Table 4, "d-δ-TOC" means d-δ-tocopherol, "d-α-TOC" means d-α-tocopherol and "dl-α-TOC" means dl-α-tocopherol.

TABLE 4

Degree of overall improvement of lesions of psoriasis vulgaris

| Concentration of tocopherol (wt. %) | Method of external application | Number of cases | \multicolumn{5}{c}{2 weeks after the initiation of the treatment*} | Rate of improvement % [1 + 2]/ Number of cases |
|---|---|---|---|---|---|---|---|---|
| | | | 1 | 2 | 3 | 4 | 5 | |
| 0% (only the base) (Comparison) | S. A. + O. D. T. | 37 | 1 | 3 | 6 | 25 | 2 | 10.8 |
| 0.5% d-δ-TOC (Invention) | S. A. + O. D. T. | 36 | 4 | 6 | 7 | 18 | 1 | 27.8 |
| 1% d-δ-TOC (Invention) | S. A. + O. D. T. | 23 | 2 | 4 | 2 | 14 | 1 | 26.1 |
| 3% d-δ-TOC (Invention) | S. A. + O. D. T. | 39 | 3 | 3 | 9 | 23 | 1 | 15.4 |
| 0.5% d-α-TOC (Comparison) | S. A. + O. D. T. | 12 | 0 | 0 | 3 | 9 | 0 | 0.0 |
| 0.5% dl-α-TOC (Comparison) | S. A. + O. D. T. | 12 | 0 | 0 | 4 | 8 | 0 | 0.0 |
| 3% d-α-TOC (Comparison) | S. A. + O. D. T. | 11 | 0 | 1 | 3 | 7 | 0 | 9.1 |
| 3% dl-α-TOC (Comparison) | S. A. + O. D. T. | 11 | 0 | 1 | 3 | 7 | 0 | 9.1 |

| Concentration of tocopherol (wt. %) | Method of external application | Number of cases | \multicolumn{5}{c}{4 weeks after the initiation of the treatment *} | Rate of improvement % [1 + 2]/ Number of cases |
|---|---|---|---|---|---|---|---|---|
| | | | 1 | 2 | 3 | 4 | 5 | |
| 0% (only the base) (Comparison) | S. A. + O. D. T. | 37 | 4 | 3 | 10 | 17 | 3 | 18.9 |
| 0.5% d-δ-TOC (Invention) | S. A. + O. D. T. | 36 | 13 | 9 | 7 | 7 | 0 | 61.1 |
| 1% d-δ-TOC (Invention) | S. A. + O. D. T. | 23 | 8 | 5 | 3 | 7 | 0 | 56.5 |
| 3% d-δ-TOC (Invention) | S. A. + O. D. T. | 39 | 8 | 10 | 8 | 13 | 0 | 46.2 |
| 0.5% d-α-TOC (Comparison) | S. A. + O. D. T. | 12 | 0 | 1 | 5 | 6 | 0 | 8.3 |
| 0.5% dl-α-TOC (Comparison) | S. A. + O. D. T. | 12 | 0 | 1 | 6 | 5 | 0 | 8.3 |
| 3% d-α-TOC (Comparison) | S. A. + O. D. T. | 11 | 0 | 1 | 5 | 6 | 0 | 9.1 |
| 3% dl-α-TOC (Comparison) | S. A. + O. D. T. | 11 | 0 | 2 | 4 | 5 | 0 | 18.2 |

*1 (The lesions disappeared or remarkably improved)
2 (Fairly improved)
3 (Slightly improved)
4 (Unchanged)
5 (Rather worsened)

It is understood from Table 4 that d-δ-tocopherol, according to the present invention, is remarkably effective for the treatment of psoriasis vulgaris.

It is apparent from Table 4 that d-δ-tocopherol, used in the present invention, exhibits a degree of significant improvement far higher than those of α-tocopherols, such as d-α-tocopherol and dl-α-tocopherol which are typical compounds possessing vitamin E activity. The rate of improvement obtained with d-δ-tocopherol of the present invention including cases of up to the ranking of "slightly improved", i.e., rankings (1+2+3), can be as high as about 70–80% of the total number of cases treated.

It is apparent from Tables 2–4 that δ-tocopherol, of the present invention, is a quite excellent medicine for treatment of psoriasis.

δ-Tocopherol and esters thereof, according to the present invention, are free of the disadvantages of the conventional corticosteroids for external use, such as the frequent reoccurrence of psoriasis and unsuitability for long-term therapy because of various unfavorable side effects. Thus, δ-tocopherol is a superior agent for preventing or treating psoriasis.

The medicine of the present invention can be used in combination with a conventional medicine for psoriasis, if necessary.

Some of the preparations of the present invention will be set forth below. The present invention is not limited to these specific compositions.

| Preparation 1 | |
|---|---|
| d-δ-Tocopherol | 0.5g |
| Ethyl p-hydroxybenzoate | 0.025g |
| Propyl p-hydroxybenzoate | 0.015g |
| Sodium laurylsulfate | 1.5g |
| Polyoxyethylene stearyl alcohol ether | 2.0g |
| Stearyl alcohol | 17.0g |
| Propylene glycol | 10.0g |
| Stearic acid | 4.0g |
| Citric acid | 0.006g |
| Purified water | ad 100.0g |

A hydrophilic ointment containing 0.5% of d-δ-tocopherol is prepared from the above components.

| Preparation 2 | |
|---|---|
| dl-δ-Tocopherol acetate | 0.6g |
| Methyl p-hydroxybenzoate | 0.025g |
| Propyl p-hydroxybenzoate | 0.015g |
| Stearyl alcohol | 25.0g |
| White petrolatum | 25.0g |
| Propylene glycol | 12.0g |
| Sodium laurylsulfate | 1.0g |
| Polyoxyethylene stearyl alcohol ether | 1.0g |
| Purified water | ad 100.0g |

A hydrophilic ointment containing 0.6% of dl-δ-tocopherol is prepared from the above components.

| Preparation 3 | |
|---|---|
| d-δ-Tocopherol | 0.7g |
| Liquid paraffin | 8.0g |
| Isopropyl myristate | 5.0g |
| Decyl oleate | 10.0g |
| Glyceryl monostearate | 7.0g |
| Stearic acid | 5.0g |
| Propylene glycol | 25.0g |
| Citric acid | 0.2g |
| Purified water | ad 100.0g |

A hydrophilic cream containing 0.7% of d-δ-tocopherol is prepared from the above components.

PREPARATION 4

0.5 Gram of dl-δ-tocopherol is mixed with 95 g of ethyl alcohol and 4.5 g of purified water. A small amount of a perfume is added to the mixture to obtain a liquid to be applied to the affected parts.

| Preparation 5 | |
| --- | --- |
| d-δ-Tocopherol | 0.5g |
| Purified lanolin | 5.0g |
| Bleached beeswax | 5.0g |
| White petrolatum | 89.5g |

An ointment is prepared from the above components.

The embodiments of the invention in which an exclusive property or privilege is claimed are defined as follows:

1. A method for treating psoriasis which comprises topically applying to a patient affected with psoriasis a composition including as the principal active ingredient, an effective amount of δ-tocopherol, dispersed or dissolved in a pharmaceutically acceptable topical carrier.

2. A method as claimed in claim 1 in which the amount of said active ingredient is from 0.1 to 5 wt.%, based on the weight of said composition.

3. A method as claimed in claim 1 in which the amount of said active ingredient is from 0.5 to 3 wt.%, based on the weight of said composition.

4. A method as claimed in claim 1 in which the amount of said active ingredient is about 0.5 wt.%, based on the weight of said composition.

5. A method as claimed in claim 1 in which said principal active ingredient is d-δ-tocopherol.

* * * * *